United States Patent [19]

Brenner et al.

[11] 4,291,037

[45] * Sep. 22, 1981

[54] 7-(OXOALKYL)-1,3-DI-N-ISO-PROPYL XANTHINES AND THEIR PRODUCTION

[75] Inventors: Günther Brenner, Erkrath-Unterbach; Joachim Goring, Gronau; Eskendar Ali Khan, Gronau; Oskar Rohte, Gronau; Manfred Tauscher, Gronau, all of Fed. Rep. of Germany

[73] Assignee: Johann A. Wulfing, Fed. Rep. of Germany

[*] Notice: The portion of the term of this patent subsequent to Dec. 30, 1997, has been disclaimed.

[21] Appl. No.: 45,381

[22] Filed: Jun. 4, 1979

Related U.S. Application Data

[63] Continuation of Ser. No. 943,815, Sep. 19, 1978, which is a continuation of Ser. No. 753,931, Dec. 23, 1976, abandoned, which is a continuation of Ser. No. 542,449, Jan. 20, 1975, abandoned.

[30] Foreign Application Priority Data

Jan. 24, 1974 [DE] Fed. Rep. of Germany ....... 2402908

[51] Int. Cl.$^3$ ............................................ C07D 473/08
[52] U.S. Cl. ..................................... 424/253; 544/271
[58] Field of Search ......................... 544/271; 424/253

[56] References Cited

U.S. PATENT DOCUMENTS 2,756,229  7/1956  Stoll et al. .......................... 260/256
3,737,433  6/1973  Mohler et al. ...................... 260/256

Primary Examiner—Nicholas S. Rizzo
Attorney, Agent, or Firm—Jacobs & Jacobs

[57] ABSTRACT 7-(Oxoalkyl)-1,3-dialkyl xanthines whose substituents in the 1- and 3-positions are alkyl groups of 2 to 6 carbons, cyclohexyl, alkoxyalkyl or hydroxyalkyl, such as 7-(3-oxobutyl)-1,3-di-n-butylxanthine, are effective vasodilators, having a marked activity in promoting blood flow through skeletal muscle, while at the same time exhibiting low toxicity.

18 Claims, No Drawings

7-(OXOALKYL)-1,3-DI-N-ISO-PROPYL XANTHINES AND THEIR PRODUCTION

CROSS-REFERENCE

This is a continuation of Ser. No. 943,815 filed Sept. 19, 1978, which is a continuation of Ser. No. 753,931 filed Dec. 23, 1976, now abandoned which is a continuation of Ser. No. 542,449 filed Jan. 20, 1975, now abandoned.

DISCLOSURE

The preparation of 7-(oxoalkyl)-1,3-dimethyl xanthines is described in DT-AS 1,233,405. These compounds are described as effective, substantially non-toxic vasodilators. In addition, the preparation of 1-(oxoalkyl)-3,7-dimethyl xanthines is known from DT-AS No. 1,235,320. These compounds are also significant vasodilators.

It has now been found that certain, hitherto unknown 7-(oxoalkyl)-1,3-dialkyl xanthines are very effective in increasing blood flow through skeletal muscle whilst at the same time showing low toxicity.

Accordingly, the present invention relates to 7-(oxoalkyl)-1,3-dialkyl xanthines corresponding to the general formula

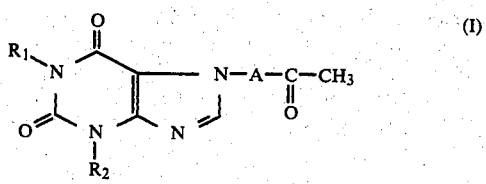
(I)

in which $R_1$ and $R_2$ are the same and/or different and represent straight-chain or branched alkyl radicals with 2 to 6 carbon atoms, cyclohexyl, alkoxyalkyl and hydroxyalkyl radicals, and A represents a hydrocarbon radical with up to 4 carbon atoms which may be substituted by a methyl group.

Suitable alkyl groups include ethyl, propyl, isopropyl, butyl, sec-butyl, tert-butyl, amyl, hexyl and the like. Alkoxy substituted alkyl groups are those containing from 2 to 6 carbons in the combined alkoxy and alkyl groups, including methoxymethyl, amyloxymethyl, methoxyethyl, butoxyethyl, propoxypropyl and the like. Hydroxyalkyl groups are those containing from 1 to 6 carbons, such as hydroxymethyl, hydroxyethyl, hydroxypropyl, hydroxyhexyl, and the like.

The hydrocarbon groups represented by A are divalent saturated aliphatic hydrocarbon groups, i.e., methylene, ethylene, trimethylene and tetramethylene, which may be substituted on the carbon adjacent the carbonyl group with methyl. Such methyl-substituted groups include ethylidene, 1,2-propylene, and 1,3-butylene.

The claimed compounds are prepared in known manner at elevated temperature, optionally in the presence of a solvent, either (a) by reacting correspondingly substituted 1,3-dialkyl xanthines corresponding to the general formula

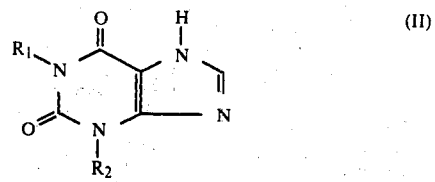
(II)

in which $R_1$ and $R_2$ are as defined above, with $\alpha,\beta$-unsaturated methyl ketones corresponding to the general formula

(III)

in which R represents hydrogen or a methyl group, in alkaline medium at elevated temperature, or (b) by reacting alkali metal salts of 1,3-dialkyl xanthine derivatives of general formula II, in which $R_1$ and $R_2$ are as defined above, with oxoalkyl halides corresponding to the general formula

(IV)

in which A is as defined above and Hal represents a halogen atom, preferably chlorine or bromine.

The described reactions are preferably carried out at temperatures in the range from 40° to 80° C., optionally under elevated or reduced pressure, but usually at atmospheric pressure. The individual starting compounds may be used either in stoichiometric quantities or in excess. The alkali salts in reaction (b) may either be prepared beforehand or in the reaction itself.

Suitable solvents are water-miscible compounds, preferably lower alcohols such as methanol, propanol, isopropanol, and various butanols, also acetone, pyridine, triethylamine, polyhydric alcohols such as ethylene glycol, and ethylene glycol monomethyl/(ethyl) ether.

The compounds prepared in accordance with the invention are distinguished by their marked effect in increasing blood flow through skeletal muscle and by their low toxicity. The most active of the compounds prepared in accordance with the invention is 7-(3-oxobutyl)-1,3-di-n-butyl xanthine.

Accordingly, the invention also relates to medicaments containing a compound of formula I as active principle. The tests described hereinafter demonstrate this activity. They were carried out with male and female cats (under urethanechloralose anaesthesia). The compounds were applied intraduodenally in methyl cellulose suspension. Blood pressure, heart rate and blood flow were determined in the usual way using a Statham transducer and heat-conduction probes. The data obtained (cf. Table I) demonstrate the marked activity of the compounds according to the invention in promoting blood flow through skeletal muscle. In this respect, the compounds according to the invention are far superior to the comparison compounds used, for example pentoxy phylline (cf. Table II). The ratio between the increase in blood flow through skeletal muscle and the increase in heart rate is favorable. The results obtained are graphically recorded in FIGS. 1 and 2.

TABLE I

7-(3-Oxobutyl)-1,3-di-n-butylxanthine

| Blood pressure (Bp) | in cats change in % | Duration in minutes |
|---|---|---|
| 5 mg/kg | +10.5 | 38.8 |
| 12.6 mg/kg | +9.7 | 57.3 |
| 31.5 mg/kg | +9.7 | 40.0 |
| 63.0 mg/kg | −7.7 | 25.0 |
| Heart rate (HR) | change in % | Duration in minutes |
| 7 mg/kg | +12.7 | >49.0 |
| 12.6 mg/kg | +13.8 | 55.9 |
| 31.5 mg/kg | +7.1 | 61.0 |
| 63.0 mg/kg | −0.9 | 40.0 |
| Skeletal muscle heat-transfer coefficient | change in % | Duration in minutes |
| 5 mg/kg | +28.8 | 72.0 |
| 12.6 mg/kg | +29.3 | 77.0 |
| 31.5 mg/kg | +24.5 | 75.0 |
| 63.0 mg/kg | +12.0 | 26.0 |

N = 6 in all dosages

TABLE II

Pentoxyphylline in cats

| Blood Pressure (Bp) | in cats change in % | Duration in minutes |
|---|---|---|
| 5 mg/kg | ±0 | — |
| 10 mg/kg | +3 | 10 |
| 30 mg/kg | +3 | 19 |
| 50 mg/kg | −3 | >28 |
| Heart rate (HR) | change in % | Duration in minutes |
| 5 mg/kg | +9 | >27 |
| 10 mg/kg | +10 | >30 |
| 30 mg/kg | +20 | >21 |
| 50 mg/kg | +10 | >26 |
| Skeletal muscle heat-transfer coefficient | change in % | Duration in minutes |
| 5 mg/kg | +10 | 20 |
| 10 mg/kg | +4 | 12 |
| 30 mg/kg | +2 | 17 |
| 50 mg/kg | ±0 | — |

The influence on the $pO_2$, $pCO_2$ and pH of arterial and venous blood was investigated in bastard dogs (under urethanechloralose anaesthesia). To this end, blood was taken from the A. aorta and from the V. femoralis at intervals of 5 minutes.

The test compounds, namely 7-(3-oxobutyl)-1,3-di-n-butyl xanthine and, for comparison, pentoxy phylline, were administered intravenously.

The results are graphically recorded in FIGS. 3 and 4.

The intravenous administration in a single dose of 30 mg of 7-(3-oxobutyl)-1,3-di-n-butyl xanthine per kg shows that this compound distinctly increases the $pO_2$ both in the arterial side and also in the venous side of the circuit for a period of 70 minutes at least. This increase in $pO_2$ is more persistent than the increase produced with pentoxy phylline.

The $LD_{50}$ of the compound in mice is more than 1000 mg/kg per os and 134 mg/kg i.v.

The vivo tests on the brains of rats showed an increased consumption of oxygen after a single dose of 100 mg/kg of 7-(3-oxobutyl)-1,3-di-n-butyl xanthine p.o. by comparison with a control with methyl cellulose suspension (cf. Table III and FIG. 5).

Examination of parmeters from fat and carbohydrate metabolism shows that the compound does not have the usual properties of xanthine derivatives, such as increasing lipolysis and increasing the glucose and lactate level in the blood of normal rats, and intensifying the adrenalin effect. On the contrary, the above-mentioned parameters are in some cases significantly reduced and the changes brought about by adrenalin even further intensified by the administration of 7-(3-oxobutyl)-1,3-di-n-butyl xanthine (cf. Tables IV to VI).

The other compounds according to the invention show equally marked pharmacological activity.

TABLE III $\mu l$ $O_2$ - consumption of fresh weight of rat's brain in vivo (in methyl cellulose suspension)
+ 100 mg/kg of 7-(3-oxobutyl)-1,3-di-n-butylxanthine p.o. 2 hrs. before killing

| Animal No. ♀ | Weight g | 10 mins. | 20 mins. | 30 mins. | 40 mins. | 50 mins. | 60 mins. |
|---|---|---|---|---|---|---|---|
| 1 | 172 | −250.7 | −458.3 | −654.3 | −831.8 | −970.1 | −1132.0 |
| 2 | 186 | −207.5 | −407.6 | −596.5 | −763.8 | −920.1 | −1105.3 |
| 3 | 177 | −275.0 | −520.3 | −728.4 | −921.7 | −1100.1 | −1189.3 |
| 4 | 176 | −183.0 | −426.8 | −602.0 | −754.5 | −914.5 | −1059.3 |
| 5 | 187 | −197.9 | −395.6 | −586.4 | −752.9 | −915.6 | −1064.4 |
| 6 | 176 | −197.1 | −370.3 | −546.9 | −699.8 | −862.9 | −995.3 |
| 7 | 205 | −220.1 | −429.7 | −606.8 | −763.1 | −940.9 | −1083.6 |
| 8 | 200 | −209.7 | −349.6 | −535.0 | −698.7 | −850.7 | −1014.9 |
| 9 | 198 | −233.3 | −438.2 | −646.7 | −805.7 | −978.8 | −1109.6 |
| 10 | 196 | −224.6 | −436.9 | −649.2 | −861.6 | −1012.6 | −1269.9 |
| 0/ | 187 | −219.9 | −423.3 | −614.3 | −785.4 | −946.6 | −1102.4 |
| % | | 3.6 | 4.3 | 3.8 | 4.2 | 4.4 | 10.2 |
| signifi-cance | | — | — | — | — | — | p <0.01 |

Control
(methyl cellulose suspension p.o.)

| 1 | 184 | −217.7 | −428.7 | −598.6 | −757.8 | −945.8 | −1024.8 |
|---|---|---|---|---|---|---|---|
| 2 | 162 | −220.5 | −404.6 | −580.0 | −750.7 | −918.4 | −1004.9 |
| 3 | 175 | −235.7 | −484.6 | −683.8 | −908.2 | −1026.9 | −1106.8 |
| 4 | 165 | −213.5 | −388.2 | −575.8 | −737.5 | −899.2 | −989.8 |
| 5 | 166 | −194.3 | −388.7 | −556.2 | −690.2 | −817.5 | −931.5 |
| 6 | 185 | −192.5 | −358.4 | −544.2 | −703.5 | −829.6 | −929.2 |
| 7 | 202 | −207.2 | −393.7 | −594.0 | −759.7 | −918.6 | −1015.3 |
| 8 | 181 | −184.4 | −371.9 | −520.6 | −698.4 | −834.3 | −973.4 |
| 9 | 179 | −245.0 | −424.9 | −638.7 | −787.5 | −942.7 | −1030.4 |
| 10 | 192 | −211.1 | −415.3 | −626.3 | −746.9 | −930.9 | −997.7 |
| φ | 179 | −212.2 | −405.9 | −591.8 | −754.0 | −906.4 | −1000.4 |

TABLE IV 7-(3-Oxobutyl)-1,3-di-n-butylxanthine glucose level
Rats: starve for 5 hours, anaesthetise with ether, cardiac puncture
Method: Bochringer test kit

| | Animal No. δ | Weight g | $E_1$ | $E_2$ | $E_2-E_1$ | mg % |
|---|---|---|---|---|---|---|
| I. Normal | 1 | 181 | 0.055 | 0.186 | 0.131 | 113.18 |
| (Methyl cellulose- | 2 | 176 | 0.062 | 0.200 | 0.138 | 119.23 |
| suspension p.c.) | 3 | 183 | 0.061 | 0.213 | 0.152 | 131.33 |
| $2^h$ before killing | 4 | 168 | 0.064 | 0.182 | 0.118 | 101.95 |
| φ 117.07 | 5 | 172 | 0.057 | 0.207 | 0.150 | 129.60 |
| | 6 | 170 | 0.062 | 0.186 | 0.124 | 107.14 |
| II. 7-(3-Oxobutyl)- | 1 | 178 | 0.057 | 0.189 | 0.132 | 114.05 |
| 1,3-di-n-butyl- | 2 | 188 | 0.059 | 0.184 | 0.125 | 108.00 |
| xanthine | 3 | 193 | 0.062 | 0.187 | 0.125 | 108.00 |
| 100 mg/kg p.o. | 4 | 189 | 0.062 | 0.182 | 0.120 | 103.68 |
| $2^h$ before killing | 5 | 163 | 0.058 | 0.183 | 0.125 | 108.00 |
| φ 108.72 | 6 | 198 | 0.064 | 0.192 | 0.128 | 110.59 |
| III. Adrenalin | 1 | 177 | 0.049 | 0.328 | 0.279 | 241.06 |
| 1 mg/kg i.p. | 2 | 170 | 0.062 | 0.292 | 0.230 | 198.72 |
| 30' before killing | 3 | 174 | 0.058 | 0.370 | 0.312 | 269.57 |
| | 4 | 189 | 0.057 | 0.203 | 0.146 | 126.14 |
| | 5 | 159 | 0.065 | 0.339 | 0.274 | 236.74 |
| | 6 | 173 | 0.074 | 0.242 | 0.168 | 145.15 |
| | 7 | 152 | 0.073 | 0.319 | 0.246 | 212.54 |
| | 8 | 163 | 0.077 | 0.274 | 0.197 | 170.21 |
| | 9 | 168 | 0.078 | 0.364 | 0.286 | 247.10 |
| | 10 | 168 | 0.074 | 0.296 | 0.222 | 191.81 |
| | 11 | 160 | 0.073 | 0.271 | 0.198 | 171.07 |
| φ 199.36 | 12 | 163 | 0.075 | 0.286 | 0.211 | 182.30 |
| IV. 7-(3-Oxobutyl)- | 1 | 191 | 0.056 | 0.285 | 0.229 | 197.86 |
| 1,3-di-n-butyl | 2 | 165 | 0.053 | 0.180 | 0.127 | 109.73 |
| xanthine | 3 | 185 | 0.055 | 0.251 | 0.196 | 169.34 |
| 100 mg/kg BW | 4 | 176 | 0.063 | 0.268 | 0.205 | 177.12 |
| oral | 5 | 199 | 0.070 | 0.199 | 0.129 | 111.46 |
| $2^h$ before killing | 6 | 181 | 0.069 | 0.330 | 0.261 | 225.50 |
| + | 7 | 152 | 0.068 | 0.193 | 0.125 | 108.00 |
| Adrenalin | 8 | 163 | 0.073 | 0.193 | 0.120 | 103.68 |
| 1 mg/kg i.p. | 9 | 161 | 0.064 | 0.261 | 0.197 | 170.21 |
| 30' before killing | 10 | 169 | 0.069 | 0.262 | 0.193 | 166.75 |
| p <0.05 | 11 | 162 | 0.073 | 0.296 | 0.223 | 192.67 |
| φ 159.12 | 12 | 178 | 0.083 | 0.288 | 0.205 | 177.12 |

TABLE V 7-(3-Oxobutyl)-1,3-di-n-butylxanthine - Lactate level
Rats: Starve for 5 hours, anaesthetise with ether, cardiac puncture
Method: Bochringer test kit

| | Animal No. | Weight g | $E_P$ | $E_L$ | $E_P - E_L$ | mg % |
|---|---|---|---|---|---|---|
| I. Normal | 1 | 181 | 0.312 | 0.079 | 0.233 | 21.9 |
| (Methyl cellulose- | 2 | 176 | 0.277 | 0.079 | 0.198 | 18.6 |
| suspension) | 3 | 183 | 0.345 | 0.079 | 0.266 | 25.0 |
| 4 ml/kg BW p.o. | 4 | 168 | 0.302 | 0.105 | 0.197 | 18.5 |
| $2^h$ before killing | 5 | 172 | 0.325 | 0.105 | 0.220 | 20.7 |
| | 6 | 170 | 0.358 | 0.105 | 0.253 | 23.8 |
| | 7 | 160 | 0.328 | 0.095 | 0.233 | 21.9 |
| | 8 | 164 | 0.275 | 0.095 | 0.180 | 16.9 |
| | 9 | 170 | 0.333 | 0.095 | 0.238 | 22.4 |
| | 10 | 160 | 0.415 | 0.095 | 0.320 | 30.1 |
| | 11 | 167 | 0.405 | 0.095 | 0.310 | 29.2 |
| | | | | | | φ22.6 |
| II. 7-(3-Oxobutyl)- | 1 | 178 | 0.321 | 0.079 | 0.242 | 22.8 |
| 1,3-di-n-butyl- | 2 | 188 | 0.230 | 0.079 | 0.151 | 14.2 |
| xanthine | 3 | 193 | 0.286 | 0.079 | 0.207 | 19.5 |
| 100 mg/kg BW p.o. | 4 | 189 | 0.274 | 0.105 | 0.169 | 15.9 |
| $2^h$ before killing | 5 | 163 | 0.234 | 0.105 | 0.129 | 12.1 |
| | 6 | 198 | 0.224 | 0.105 | 0.119 | 11.2 |
| | 7 | 152 | 0.242 | 0.095 | 0.147 | 13.8 |
| | 8 | 157 | 0.252 | 0.095 | 0.157 | 14.8 |
| | 9 | 153 | 0.355 | 0.095 | 0.260 | 24.5 |
| | 10 | 149 | 0.274 | 0.095 | 0.179 | 16.8 |
| p <0.01 | 11 | 172 | 0.235 | 0.095 | 0.140 | 13.2 |
| | | | | | | φ 16.2 |
| II. Adrenalin | 1 | 189 | 0.730 | 0.079 | 0.651 | 61.3 |
| 1 mg/kg BW i.p. | 2 | 194 | 0.345 | 0.105 | 0.240 | 22.6 |
| 30' before killing | 3 | 159 | 0.768 | 0.105 | 0.663 | 62.4 |
| | 4 | 173 | 0.631 | 0.105 | 0.526 | 49.5 |
| | 5 | 148 | 0.763 | 0.105 | 0.658 | 61.9 |
| | 6 | 156 | 0.495 | 0.105 | 0.390 | 36.7 |
| | | | | | | φ 49.0 |
| V. 7-(3-Oxobutyl)-1,3-di- | 1 | 191 | 0.638 | 0.079 | 0.559 | 52.6 |
| n-butylxanthine | 2 | 165 | 0.506 | 0.079 | 0.427 | 40.2 |
| 100 mg/kg BW p.o. | 3 | 185 | 0.622 | 0.079 | 0.543 | 51.1 |
| $2^h$ before killing | 4 | 176 | 0.850 | 0.105 | 0.745 | 70.1 |
| + | | | | | | |
| Adrenalin | 5 | 199 | 0.552 | 0.105 | 0.447 | 42.1 |
| 1 mg/kg BW i.p. | 6 | 181 | 0.705 | 0.105 | 0.600 | 56.5 |
| 30' before killing | | | | | | φ 52.1 |

TABLE VI

Serum fatty acids FFS
Rats ♂, starve for 17 h., anaesthetise with ether, cardiac puncture
7-(3-Oxobutyl-1,3-di-n-butylxanthine 160 mg/kg
Method: Acta Biol. Vol. 12, p. 520 (1964)

|  | Animal No. | Weight g | μ val/ml |
|---|---|---|---|
| Control series | 1 | 151 | 1.12 |
| (methyl cellulose- | 2 | 155 | 0.99 |
| suspension) | 3 | 160 | 0.87 |
| 4 mg/kg BW p.o. | 4 | 175 | 0.87 |
| 2ʰ before killing | 5 | 168 | 0.81 |
|  | 6 | 160 | 0.73 |
|  | 7 | 213 | 0.72 |
|  | 8 | 200 | 0.76 |
|  | 9 | 160 | 1.10 |
|  | 10 | 150 | 0.99 |
|  | φ | 169 | 0.90 |
| 7-(3-Oxobutyl)-1,3-di-n- | 1 | 151 | 0.68 |
| butylxanthine | 2 | 152 | 0.76 |
| 160 mg/kg BW p.o. | 3 | 152 | 0.75 |
| 2ʰ before killing | 4 | 188 | 0.57 |
|  | 5 | 165 | 0.81 |
|  | 6 | 170 | 0.96 |
|  | 7 | 190 | 1.07 |
|  | 8 | 190 | 1.02 |
|  | 9 | 190 | 0.95 |
|  | 10 | 184 | 0.90 |
|  | 11 | 203 | 1.02 |
|  | 12 | 152 | 1.14 |
|  | φ | 174 | 0.89 |
| Adrenalin | 1 | 161 | 1.23 |
| 1 mg/kg BW i.p. | 2 | 152 | 1.36 |
| 30' before killing | 3 | 177 | 1.09 |
|  | 4 | 173 | 1.17 |
|  | 5 | 172 | 1.17 |
|  | 6 | 167 | 1.10 |
|  | 7 | 139 | 1.52 |
|  | 8 | 133 | 1.60 |
|  | 9 | 149 | 1.73 |
|  | 10 | 147 | 1.49 |
|  | 11 | 140 | 1.45 |
|  | 12 | 142 | 1.31 |
|  | φ | 154 | 1.35 |
| 2-(3-Oxobutyl)-1,3-di-n- | 1 | 160 | 0.84 |
| butylxanthine | 2 | 152 | 0.99 |
| 160 mg/kg BW p.o. | 3 | 150 | 0.96 |
| 2ʰ before killing | 4 | 168 | 1.28 |
| + | 5 | 160 | 1.86 |
| Adrenalin | 6 | 181 | 1.39 |
| 1 mg/kg BW i.p. | 7 | 166 | 1.72 |
| 30' before killing | 8 | 146 | 1.46 |
|  | 9 | 142 | 1.67 |
|  | 10 | 143 | 1.65 |
|  | φ | 157 | 1.33 |

The invention is illustrated by the following Examples.

EXAMPLE 1

7-(3-oxobutyl)-1,3-di-n-butyl xanthine 264.8 g (1 mol) of 1,3-di-n-butyl xanthine, 84 g (1.2 mol) of methyl vinyl ketone, 1060 ml of methanol and 39.7 ml of triethylamine are introduced into a 3 liter capacity three-necked flask, and the mixture slowly heated with stirring to 40° to 45° C. The reaction solution is then kept at that temperature until hardly any 1,3-di-n-butyl xanthine can be detected by thin-layer chromatography. Reaction time, approximately 2 to 2.5 hours.

On completion of the reaction, water is added to this solution in small portions in such a quantity that an approximately 75 to 80% aqueous methanolic solution is formed. This solution is left standing for several hours in a refrigerator and the crystals formed are filtered off under suction. Another recrystallization from methanol-water gives 276 g ($\triangleq$80% of the theoretical) of 7-(3-oxobutyl)-1,3-di-n-butyl xanthine melting at 86° to 87° C.

Another 24 g of 7-(3-oxobutyl)-1,3-di-n-butyl xanthine are obtained by concentrating the methanolic mother liquors. Total yield: 300 g $\triangleq$ 87% of the theoretical

| Analysis: | C | H | N | O |
|---|---|---|---|---|
| Calculated: | 61.06 | 7.84 | 16.75 | 14.35% |
| Found: | 60.92 | 7.81 | 16.96 | 14.34% |

The compounds listed in Table VII below are similarly obtained by modification (a) of the claimed process.

TABLE VII

| Example No. | $R_1$ | $R_2$ | Starting Material R | A | Melting point °C.: recrystallisation solvent | Yield % of theoretical | Combustion analysis: C | H | N | O |
|---|---|---|---|---|---|---|---|---|---|---|
| 1 | n-C₄H₉— | n-C₄H₉— | —H | —CH₂—CH₂— | 86–87 methanol/water | 87 | +61.06 ++60.92 | 7.84 7.81 | 16.75 16.96 | 14.35 14.34 |
| 2 | n-C₄H₉— | n-C₄H₉— | —CH₃ | —CH—CH₂— \| CH₃ | 46 petrol/ethanol | 79 | +62.05 ++62.20 | 8.10 8.13 | 16.08 16.02 | 13.78 13.52 |
| 3 | —CH—(CH₃)₂ | —CH—(CH₃)₂ | —CH₃ | —CH—CH₂— \| CH₃ | 91 petrol | 77 | +59.98 ++60.15 | 7.55 7.39 | 17.49 17.24 | 14.98 15.40 |
| 4 | —CH—(CH₃)₂ | —CH—(CH₃)₂ | —H | —CH₂—CH₂— | 73 ethanol | 80 | +58.81 ++59.13 | 7.24 7.28 | 18.29 18.09 | 15.67 15.52 |

(calc: +)
(found: ++)

EXAMPLE 5

7-(5'-oxohexyl)-1,3-dibutyl xanthine 21.5 g (0.12 mol) of freshly distilled 1-bromo-5-hexanone are dissolved in 200 ml of absolute ethanol in a 500 ml capacity flask, followed by the gradual dropwise addition at boiling temperature of 34.7 g (0.12 mol) of sodium 1,3-dibutyl xanthine dissolved in 200 ml of absolute ethanol. The solution is heated under reflux. The reaction is over after about 24 hours. Removal of the alcohol by distillation in a rotary evaporator leaves a solid white residue. This residue is introduced into an extraction tube in which it is extracted with petrol 40/80 in a Soxhlet apparatus until no more starting material can be detected. The petrol is distilled off in a rotary evaporator, leaving 25 g (0.069 mol) of 7-(5'-oxohexyl)-1,3-dibutyl xanthine, corresponding to 75% of the theoretical, based on the sodium 1,3-dibutyl xanthine reacted.

The crude product has a melting point of 80° to 82° C.

Pure 7-(5'-oxohexyl)-1,3-dibutyl xanthine melting at 88° C. is obtained by repeated recrystallization from isopropanol. $C_{19}H_{30}N_4O_3$(362.74)

|  | C | H | N | O |
|---|---|---|---|---|
| Calculated: | 62.96 | 8.34 | 15.48 | 13.24% |
| Found: | 62.99 | 8.14 | 15.34 | 13.40% |

The extraction residue is dissolved in ethanol and the resulting solution separated off from the sodium bromide. The solution is then concentrated to dryness and the residue recrystallized from ethanol. 75. g (0.0284 mol) of 1.3-dibutyl xanthine are recovered.

The compounds listed in Table VIII are similarly prepared by modification (b) of the claimed process.

We claim:

1. 7-(1-methyl-3-oxobutyl)-1,3-di-isopropyl xanthine.
2. The compound of claim 1 in solid form.
3. The compound of claim 1 in essentially pure form.
4. 7-(3-oxobutyl)-1,3-di-n-isopropyl xanthine.
5. The compound of claim 4 in solid form.
6. The compound of claim 4 in essentially pure form.
7. 7-(5-oxohexyl)-1,3-di-isopropyl xanthine.
8. The compound of claim 7 in solid form.
9. The compound of claim 7 in essentially pure form.
10. 7-(1-methyl-2-oxopropyl)-1,3-di-isopropyl xanthine.
11. The compound of claim 10 in solid form.
12. The compound of claim 10 in essentially pure form.
13. A pharmaceutical composition useful for promoting the flow of blood through skeletal muscles in humans and animals which comprises a therapeutically effective amount of 7-(1-methyl-3-oxobutyl)-1,3-di-isopropyl xanthine in combination with a pharmaceutically acceptable carrier.
14. A pharmaceutical composition useful for promoting the flow of blood through skeletal muscles in humans and animals which comprises a therapeutically effective amount of 7-(3-oxobutyl-1,3-di- n-isopropyl xanthine in combination with a pharmaceutically acceptable carrier.
15. A pharmaceutical composition useful for promoting the flow of blood through skeletal muscles in humans and animals which comprises a therapeutically effective amount of 7-(5-oxohexyl)-1,3-di-isopropyl xanthine in combination with a pharmaceutically acceptable carrier.
16. A method of promoting the flow of blood through skeletal muscles in humans and animals which comprises administering to a human or animal in need thereof a therapeutically effective amount of 7-(1-methyl-3-oxobutyl)-1,3-di-isopropyl xanthine.
17. A method of promoting the flow of blood through skeletal muscles in humans and animals which comprises administering to a human or animal in need thereof a therapeutically effective amount of 7-(3-oxobutyl)-1,3-di-n-isopropyl xanthine.
18. A method of promoting the flow of blood through skeletal muscles in humans and animals which comprises administering to a human or animal in need thereof a therapeutically effective amount of 7-(5-oxohexyl)-1,3-di-isopropyl xanthine.

* * * * *

UNITED STATES PATENT AND TRADEMARK OFFICE
CERTIFICATE OF CORRECTION

PATENT NO. : 4,291,037
DATED : Sep. 22, 1981
INVENTOR(S) : Brenner et al.

It is certified that error appears in the above-identified patent and that said Letters Patent are hereby corrected as shown below:

Title page, item [30], please correct the priority date.

It should read: Jan. 22, 1974

Signed and Sealed this

Sixteenth Day of April 1985

[SEAL]

Attest:

DONALD J. QUIGG

Attesting Officer     Acting Commissioner of Patents and Trademarks